United States Patent [19]

Bettarini et al.

[11] Patent Number: 5,286,725
[45] Date of Patent: Feb. 15, 1994

[54] PYRIDAZINONES ENDOWED WITH ACARICIDE AND INSECTICIDE ACTION

[75] Inventors: Franco Bettarini; Luigi Capuzzi, both of Novara; Sergio Massimini, Milan; Paolo Castoro, Vercelli; Vincenzo Caprioli, Pavia, all of Italy

[73] Assignee: Ministero Dell'Universita' E Della Ricerca Scientifica E Technologica, Rome, Italy

[21] Appl. No.: 930,451

[22] Filed: Aug. 19, 1992

Related U.S. Application Data

[63] Continuation of Ser. No. 760,374, Sep. 16, 1991, abandoned.

[30] Foreign Application Priority Data

Sep. 17, 1990 [IT] Italy .................. 21496A/90

[51] Int. Cl.$^5$ ............................. A01N 43/58
[52] U.S. Cl. ...................... 514/247; 544/240
[58] Field of Search .................. 544/240; 514/247

[56] References Cited

U.S. PATENT DOCUMENTS

| | | | |
|---|---|---|---|
| 4,820,704 | 4/1989 | Richarz et al. | 544/240 |
| 4,945,091 | 7/1990 | Makabe et al. | 544/240 |
| 5,004,744 | 4/1991 | Weismuller et al. | 544/240 |
| 5,026,850 | 6/1991 | Taniguchi et al. | 544/240 |
| 5,063,232 | 11/1991 | Leyendecker | 514/247 |
| 5,169,848 | 12/1992 | Bettarini | 544/240 |

FOREIGN PATENT DOCUMENTS

| | | |
|---|---|---|
| 35946 | 7/1989 | Australia . |
| 2005279 | 6/1990 | Canada . |
| 0344684 | 12/1989 | European Pat. Off. . |
| 0377892 | 7/1990 | European Pat. Off. . |
| 3733220 | 4/1989 | Fed. Rep. of Germany . |

OTHER PUBLICATIONS

Leyendecker et al., Chem. Abstr., vol. 114, Entry 6527(w) (1990) Abstracting DE 3844227.

Primary Examiner—Donald G. Daus
Attorney, Agent, or Firm—Oblon, Spivak, McClelland, Maier & Neustadt

[57] ABSTRACT

There are described new pyridazinones endowed with acaricide and insecticide action, having general formula (I):

$$(CH_3)_3C-N-N=CH-C(S-Z-R)=C(X)-C(=O)- \text{(I)}$$

wherein X is halo or alkyl, Z is alkylene and R is substituted cyclohexyl or cyclohexenyl.

3 Claims, No Drawings

PYRIDAZINONES ENDOWED WITH ACARICIDE AND INSECTICIDE ACTION

This is a continuation of application Ser. No. 07/760,374, filed on Sep. 16, 1991, now abandoned.

The present invention relates to new derivatives of 3(2H)-pyridazinone, the processes for preparing them, the acaricide and insecticide compositions containing the new compounds and the use of said compositions for controlling acari, insects and ticks.

In particular, the invention relates to a new class of substituted pyridazinones exhibiting an increased efficacy in controlling particularly acari and insects which are noxious in the agrarian, civil and zootechnical fields.

3(2H)-pyridazinones having fungicide, insecticide, acaricide and nematocide actions are described in European patent applications 88384, 134439, 183212, 199281, 232825, 283271, 302346, 320733 and in German patent application DE-3733220.

In the last cited patent application there are described compounds of general formula (A):

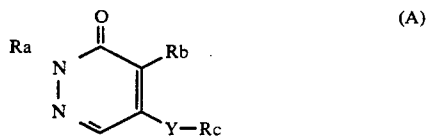

wherein Ra represents H or a $C_1-C_6$ alkyl group (optionally substituted with halogens or CH), Rb represents H, an alkyl or a halogen, Y represents O or S, Rc represents a $C_1-C_{20}$ alkyl group, optionally substituted. Among the possible substituents of the $C_1-C_{20}$ alkyl group we consider $C_3-C_8$ cycloalkyl groups optionally substituted with OH or $C_1-C_4$ alkylcarbonyloxy groups.

The pyridazinones of the present invention, having general formula (I), defined hereinafter, are substituted in position 5 of the pyridazinone nucleus with cyclohexylalkylthio or cyclohexenylalkylthio groups, which are substituted in turn, preferably in position 4 of the cycle, with specific groupings. Said compound are endowed, in particular, with a much higher acaricide action as compared with the compounds described in said German patent application 3733220.

Thus, object of the present invention are the new pyridazinones having general formula (I):

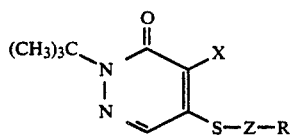

wherein:
X represents a halogen or a straight or branched $C_1-C_4$ alkyl group;
Z represents a $C_1-C_3$ alkylene optionally substituted with halogen or with $C_1-C_3$ alkyl or haloalkyl groups;
R represents a cyclohexyl or a cyclohexenyl substituted, preferably in position 4, with $C_1-C_6$ alkyl or alkoxyl groups, with $C_2-C_7$ alkoxyalkyl or alkylthioalkyl groups, with $C_2-C_7$ alkenyl groups, with $C_3-C_8$ alkoxyalkoxyl, cycloalkyl or cycloalkoxyl groups, with $C_4-C_9$ alkoxyalkoxyalkyl, cycloalkylalkyl, cycloalkylalkoxyl or cycloalkoxyalkyl groups, with $C_5-C_{10}$ cycloalkylalkoxyalkyl groups, optionally substituted, with halogen atoms.

The compounds of general formula (I) are endowed with a high acaricide and insecticide activity towards acari and noxious insects in the agrarian, civil and zootechnical fields; in particular they exert their action against important species of tetranids, hemiptera, lepidopters, coleopters, dipterans, blattodeas, ixodids.

The compounds of general formula (I) are prepared by reacting a pyridazinone of formula (II) with a compound of formula (III) according to the reaction scheme 1:

Scheme 1

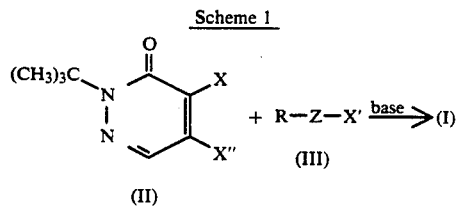

In these formulas, the symbols X, R and Z refer to the substituents as described hereinbefore; X' and X" represent a Cl, Br or I atom, or a SH group, provided that one out of them consists of a SH group and the other of Cl, Br or I.

The reaction is preferably conducted in an inert organic solvent such as for example benzene, toluene, acetone, methylethylketone, acentonitrile, dioxane, N,N-dimethylformamide, dimethylsulphoxide, in the presence of an inorganic base such as e.g. sodium hydride, potassium hydroxide, calcium hydroxide, sodium carbonate, potassium carbonate, or in the presence of an organic base, such as for example triethylamine or pyridine, in the range from room temperature to the boiling temperature of the solvent employed in the reaction.

The compounds of formula (II) are described in literature; they are prepared according to what is reported for example in "Advances in Heterocyclic Chemistry" vol. 9, pages 235-236 and 249-258, Ed. A. R. Katritzky, A. J. Boulton, Academic Press, New York and London 1968, and cited reference.

The intermediates of formula (III), if not known by themselves, can be prepared according to methodologies belonging to the usual practice of the organic chemistry.

The compounds of general formula (I) can be in the form of mixtures of isomers, the separation of which can be carried out by using known chemical techniques such as column chromatography or thin layer chromatography.

The isolation and the use of each individual isomer, as well as the direct use of the mixtures obtainable from the preparation of the compounds and the utilization of the mixtures that come from an incomplete separation of the isomers are within the scope of the present invention.

As pointed out hereinbefore, the compounds of general formula (I) are endowed with a high insecticide and in particular acaricide action, which is exerted, in general, at all the stages of the life cycle of acari and insects (larvae, adults and eggs); furthermore they possess an excellent residual activity.

Thanks to their positive characteristics, the compounds of formula (I) are suited to be utilized for protecting against acari and noxious insects both agrarian and horticultural cultures, and environment with human beings, as well as domestic animals and cattle.

For the purpose of their practical use, both in agriculture and in other sectors, it is advantageous to use the compounds of the invention in the form of suitable compositions.

These compositions contain, besides one or more compounds of formula (I) as active product, solid inert vehicles (for example kaolin, silica, talc, attapulgite, bentonite, diatom earth, etc.) or inert liquid vehicles (organic solvents, vegetal or mineral oils, water, and mixtures thereof) and optionally other additives which are usually utilized in the formulative sector, such as surfactants, suspending agents, dispersants and wetting agents.

For particular applicative requirements or in order to extend the compositions, range of action it is possible to add other active ingredients, such as for example other insecticides or acaricides, herbicides, fungicides or fertilizers to the above-described compositions.

The applicative doses vary as a function of various factors such as the infestation type and degree, the type of utilized composition, climatic and ambiental factors.

For the practical exployment in agriculture, doses of the compound of formula (I) in the range from 5 g to 5 kg per hectare provide a satisfactory protection.

In order to better illustrate the present invention, the following examples are given.

EXAMPLE 1

Synthesis of 4-tert-butyl-cyclohex-2-enylmethyl bromide (intermediate to yield compound 1 in the example 4)

4-tert-butylcyclohexancarboxilic acid (2.76 g, 0.015 mol), cis/trans mixture 1:1, in anhydrous THF (10 cm$^3$) was added dropwise to a stirred suspension of LiAlH$_4$ (1.14 g, 0.030 mol) in anhydrous THF (10 cm$^3$), under atmosphere of nitrogen. After 2 h at room temperature the solution was thinned with ether and, under stirring, HCl (10% b.w.) was slowly added dropwise till acidic pH. The two layer were separated and the organic one was washed, then added with Na$_2$SO$_4$ and thoroughly dried under reduced pressure. The residue (2.5 g) was dissolved in anhydrous ether (10 cm$^3$), cooled to −70° C., to which was added dropwise and with stirring PBr$_3$ (1.5 g, 0.055 mol). After the addition was complete the mixture was stirred under reflux to room temperature for 2 h; ether was added and then some satured NaHCO$_3$ solution. After the two layers were separated, Na$_2$SO$_4$ was added to the organic phase which was then dried under reduced pressure. Chromatography on silica gel eluting with hexane gave 1.1 g of 4-tert-butyl-cyclohex-2-enylmethyl bromide (trans isomer) out of 2.4 g of residue. Such product was employed in the example 4.

$^1$H-NMR (60 MHz, CCl$_4$): δ0.6–2.2(m), 10H; δ0.9(s), 9H; δ3.2(d), 2H.

EXAMPLE 2

Synthesis of 4-methoxymethyl-cyclohexylmethyl bromide (intermediate to yield compound 5 in the example 8)

1,4-bis(Hydroxymethyl)cyclohexane (5 g, 0.0347 mol), cis/trans mixture 1:3, in anhydrous DMF (20 cm$^3$) was added dropwise to NaH (1.6 g, 0.0366 mol, 55%) washed with hexane, under atmosphere of nitrogen. The mixture was stirred at room temperature for ½ h, then CH$_3$I (5 g, 0.0352 mol) dissolved in DMF (20 cm$^3$) was added dropwise. After the addition was complete the solution was stirred at room temperature for 2 h; NH$_4$Cl solution was added then thoroughly extracted with ether, to which Na$_2$SO$_4$ was added and dried under reduced pressure. Chromatography on silica gel eluting with hexane/ethyl acetate (55/45) gave 4-methoxymethyl-cyclohexylmethanol (1.8 g, 0.0113 mol) out of 4.1 g of residue. Such compound was dissolved in ether (10 cm$^3$), cooled to −70° C. and was added dropwise with PBr$_3$ (1.2 g, 0.0044 mol). After the addition was complete the solution was stirred to room temperature for 2 h, was extracted with ether and cautiously added with satured NaHCO$_3$ solution. After the two layers were separated, the organic phase was added with Na$_2$SO$_4$ and dried under reduced pressure. Chromatography on silica gel eluting with hexane gave 4-methoxymethyl cyclohexylmethyl bromide, cis\ trans mixture 1\ 3. Such product was employed in the example 8.

$^1$H-NMR (60 MHz, CCl$_4$): δ0.6–2.2 (m), 10H; δ2.9–3.5 (m), 4H; δ3.25 (s), 3 H.

EXAMPLE 3

Synthesis of 4-methoxy-cyclohexylmethyl bromide (intermediate) to yield compound 20 in the example 23

4-Methoxy-cyclohexyl methanol (0.84 g, 0.0058 mol), was yielded in cis/trans mixture 65/35 according to the description in the "Journal Chemical Society", 1942, pag 326–333, was dissolved in ether (15 cm$^3$), to which PBr$_3$ (0.6 g, 0.0022 mol) was added dropwise at −70° C. with stirring. After the addition was complete the solution was stirred to room temperature for 2 h, ether was added in order to thin it and then it was thoroughly washed with saturated NaHCO$_3$ solution. After the two layers were separated, the organic phase was added with Na$_2$SO$_4$ and was dried under reduced pressure. The residue is employed as such in the preparation of the compound 20 in the example 23.

$^1$H-NMR (60 MHz, CCl$_4$): δ0.6–2.2 (m), 9H; δ3.0–3.5 (m), 3H; δ3.25–3.3 (2s), 3H.

EXAMPLE 4

Synthesis of 2-tert.butyl-4-chloro-5-(4-tert.butyl-cyclohexyl)-methylthio-3(2H)-pyridazinone (compound 1).

To a suspension of 0.22 g of potassium carbonate in 5 cc of dimethylformamide 0.4 g of trans-1-bromomethyl-4-tert.butyl-cyclohexane and 0.35 g of 2-tert.butyl-4-chloro-5-mercapto-3(2H)-pyridazinone. Were added the whole was stirred for 16 hours at room temperature, then it was thinned with ether and washed with diluted HCl and brine; it was anhydrified, the solvent was evaporated and the resulting rough product was eluted by silica gel chromatography with hexane/ethyl acetate 9/1. 0.5 g of product (M.P.=96° C.) were obtained.

$^1$H-NMR (60 MHz, C Cl$_4$); δ at 0.7–2.2 (complex, 10H), 0.8 (s,9H), 1.6 (s, 9H), 2.8 (d, 2H), 7.4 (s,1H).

EXAMPLE 5

Synthesis of 2-tert.butyl-4-chloro-5-[4-(1-methylethenyl)-cyclohex-1-enyl]methylthio-3(2H)-pyridazinone (compound 2).

To a suspension of 0.81 g of potassium carbonate in 10 ml of dimethylformamide 1.28 g of 2-tert.butyl-4-chloro-5-mercapto-3(2H)-pyridazinone and, after 15 minutes, 1 g of 4-(1-methylethenyl)cyclohex-1-enylmethyl-bromide. Were added it was stirred for 3 hours at room temperature, it was diluted with ether, then it wa washed with diluted HCl and brine; it was anhydrified, the solvent was evaporated and the rough product so obtained was eluted by silica gel chromatography with hexane/ethyl acetate 92/8. 1 g of product (M.P.=50° C.) was obtained.

$^1$H-NMR (60 MHz, CCl$_4$): δ at 1.2–2.4 (complex, 7H), 1.6 (s, 9H), 1.7 (s, 3H), 3.6 (s, 2H), 4.7 (m, 2H), 5.8 (m, 1H), 7.5 (s, 1H).

EXAMPLE 6

Synthesis of 2-tert.butyl-4-chloro-5-[4-(1,1,2-trifluoro-2-trifluoromethoxy-ethoxy)methyl-cyclohexyl]methylthio-3(2H)-pyridazinone (compound 3)

To a suspension of 0.47 g of potassium carbonate in 10 ml of dimethylformamide, 0.75 g of 2-tert.butyl-4-chloro-5-mercapto-3(2H)-pyridazinone and 1.3 g of 4-(1,1,2-trifluoro-2-trifluoromethoxyethoxy)methyl-cyclohexylmethyl-bromide. Were added it was stirred for 2 hours at room temperature, it was diluted with ether, then it was washed with diluted HCl and brine; it was anhydrified, the solvent was evaporated and the obtained rough product was eluted by silica gel chromatography with hexane/ethyl acetate 98/2. 0.65 g of a mixture of CIS/trans (15/85) product was obtained.

$^1$NMR (60 MHz, CDCl$_3$): δ at 0.8–2.1 (complex, 10H), 1.6 (s, 9H), 2.8 (m, 2H), 3.8 (m, 2H), 5.9–6.1 (dt, 1H), 7.5 (s, 1H).

EXAMPLE 7

Synthesis of 2-tert.butyl-4-chloro-5-(4-tert.butyl-cyclohex-2-enyl)-methylthio-3(2H)-pyridazinone (compound 4)

To a suspension of 350 mg of potassium carbonate in 15 ml of dimethylformamide, 0.57 g of 2-tert.butyl-4-chloro-5-mercapto-3(2H)-pyridazinone and 0.6 g of 4-tert.butyl-cyclohex-2-enylmethyl-bromide. Were added it was stirred for 4 hours at 50° C. It was diluted with ether, then it was washed with diluted HCl and brine; it was anhydrified, the solvent was evaporated, the resulting rough product was subjected to silica gel chromatography by eluting with hexane/ethyl acetate 95:5. 0.35 g of a product having a melting point of 82°–84° C. were obtained.

$^1$NMR(60 MHz, CDCl$_3$): δ at 0.9 (s, 9H), 1.15–2.50 (complex, 6H), 1.65 (s, 9H), 2.85–3.15 (m, 2H), 5.6–5.9 (complesso, 2H), 7.6 (s, 1H).

EXAMPLE 8

Synthesis of 2-tert.butyl-4-chloro-5-(4-methoxymethyl-cyclohexyl)-methylthio-3(2H)-pyridazinone (compound 5)

A mixture of 0.32 g of potassium carbonate, 0.5 of 2-tert.butyl-4-chloro-5-mercapto-3(2H)-pyridazinone and 0.5 g of 4-methoxymethyl-cyclohexyl-methyl-bromide in 10 ml of dimethylformamide was stirred at room temperature for 6 hours. It was diluted with ether, then it was washed with diluted HCl and brine; it was anhydrified, the solvent was evaporated, the resulting rough product was subjected to silica gel chromatography by eluting with hexane/ethyl acetate 85:15. 0.6 g of a mixture of (CIS/trans 20:80) products was obtained.

$^1$H-NMR (CCl$_4$): δ at 0.7–2.2 (complex, 10 H), 1.6 (s, 9H), 2.8 (m, 2H), 3.1 (m, 2H), 3.25 (s, 3H), 7.45 and 7.5 (2s, 1H).

EXAMPLE 9

Synthesis of 2-tert.butyl-4-chloro-5-(4-ethoxymethyl-cyclohexyl)-methylthio-3(2H)-pyridazinone (compound 6)

A mixture of 2-tert.butyl-4-chloro-5-mercapto-3(2H)-pyridazinone (0.65 g), 4-ethoxymethyl-cyclohexylmethyl-bromide (0.7 g) and potassium carbonate (0.41 g) in dimethylformamide (10 ml) was stirred at room temperature for 6 hours. It was diluted with ether, then it was washed with diluted HCl and brine; it was anhydrified, the solvent was evaporated and the resulting rough product was subjected to silica gel chromatography by eluting with ethane/ethyl acetate 85:15. 0.6 g of a mixture of (CIS/trans 20:80) products was obtained.

$^1$H-NMR (60 MHz, CCl$_4$): δ at 0.7–2.2 (complex, 10H), 1.1 (t, 3H), 1.6 (s, 9H), 2.8 (m, 2H), 3.1 (m, 2H), 3.3 (q, 2H), 7.4 and 7.45 (2s, 1H).

EXAMPLE 10

Synthesis of 2-tert.butyl-4-chloro-5-(4-tert.butoxymethyl-cyclohexyl-methylthio-3(2H)-pyridazinone (compound 7)

A mixture of 2-tert.butyl-4-chloro-5-mercapto-3(2H)-pyridazinone (0.5 g), 4-tert.butoxymethyl-cyclohexylmethyl-bromide (0.6 g) and potassium carbonate (0.32 g) in dimethylformamide (10 ml) was stirred at room temperature for 8 hours. It was diluted with ether, then it was washed with diluted HCl and with a saturated sodium chloride solution; it was anhydrified, the solvent was evaporated and the resulting rough product was subjected to silica gel chromatography by eluting with hexane/ethyl acetate 9:2. 0.35 g of a mixture (CIS/trans 21/79)products obtained.

$^1$H-NMR (60 MHz, CDCl$_3$): δ at 1.1 (s, 9H), 0.7–2.2 (complex, 10H), 1.6 (s, 9H), 2.8 (m, 2H), 3.05 (m, 2H), 7.35 and 7.4 (2s, 1H).

EXAMPLE 11

2-Tert-butyl-4-chloro-5-(4-isopropoxymethyl-cyclohexyl)methylthio-3(2H)-pyridazinone (compound 8)

Such compound (trans isomer) was prepared according to what is produced in the example 4 starting from 2-tert-butyl-4-chloro-5-mercapto-3(2H)-pyridazinone and trans 4-isopropoxymethylcyclohexylmethyl bromide.

$^1$H-NMR )60 MHz, CCl$_4$): δ0.6–2.2(m), 10H; δ1.05(d), 6H; δ1.55(s), 9H; δ2.85 (d), 2H; δ3.1(d), 2H; δ3.3 (m), 1H; δ7.4(s), 1H

EXAMPLE 12

2-tert-butyl-4-chlor-5-(4-isobutoxymethyl-cyclohexyl)-methylthio-3(2H)-pyridazinone (compound 9)

Such compound (cis/trans 13:87 mixture) was prepared according to what is produced in the example 4 starting from 2-tert-butyl-4-chloro-5-mercapto-3(2H)-pyridazinone and 4-isobutoxymethylcyclohexylmethyl bromide.

$^1$H-NMR (60 MHz, CCl$_4$): δ0.6–2.3(m), 11H; δ0.85(d), 6H; δ1.55(s), 9H; δ2.85(m), 2H; δ2.9–3.3(m), 4H; δ7.4(s), 1H.

EXAMPLE 13

2-tert-butyl-4-chloro-5-[4-(2,2,2-trifluoroethoxymethyl)cyclohexyl]methylthio-3(2H)-pyridazinone (compound 10)

Such compound (cis/trans 15/85 mixture) was prepared according to what is produced in the example 4 starting form 2-tert-butyl-4-chloro-5-mercapto-3(2H)-pyridazinone and 4-(2,2,2-trifluorethoxymethyl)cyclohexylmethyl bromide.

$^1$H-NMR (60 MHz, CCl$_4$): δ0.6–2.2(m), 10H; δ1.55(s), 9H; δ2.85(m), 2H; δ3.3(m),2H;δ3.7(q), 2H; δ7.4(bs), 1H.

EXAMPLE 14

2-tert-butyl-4-chloro-5-(4-cyclopropylmethoxymethylcyclohexyl) methylthio-3(2H)-pyridazinone (compound 11)

Such compound (cis/trans 14/86 mixture) was prepared according to what is produced in the example 4 starting from 2-tert-butyl-4-chloro-5-mercapto-3(2H)-pyridazinone and 4-cyclopropylmethoxymethylcyclohexylmethyl bromide.

$^1$H-NMR (60 MHz, CCl$_4$): δ0.0–0.65(m), 4H; δ0.65–2.3(m), 11H; δ1.6(s), 9H; δ2.85(m), 2H; δ3.15(m), 4H; δ7.4(s), 1H.

EXAMPLE 15

2-tert-butyl-4-chloro-5-(4-n-propoxymethylcyclohexyl) methylthio-3(2H)-pyridazinone (compound 12)

Such compound (cis/trans 17/83 mixture) was prepared according to what is produced in the example 4 starting from 2-tert-butyl-4-chloro-5-mercapto-3(2H)-pyridazinone and 4-n-propoxymethylcyclohexylmethyl bromide.

$^1$H-NMR (60 MHz, CCl$_4$): δ0.5–2.2(m), 15H; δ1.6(s), 9H; δ2.8(m), 2H; δ2.9–3.35(m), 4H; δ7.35(s), 1H.

EXAMPLE 16

2tert-butyl-4-chloro-5-(4-n-butoxymethyl-cyclohexyl)methylthio-3(2H)-pyridazinone (compound 13)

Such compound (cis/trans 15/85 mixture) was prepared according to what is produced in the example 4 starting from 2-tert-butyl-4-chloro-5-mercapto-3(2H)-pyridazinone and 4-n-butoxymethylcyclohexylmethyl bromide.

$^1$H-NMR (60 MHz, CCl$_4$): δ0.5–2.2(m), 17H; δ1.6(s), 9H; δ2.8(m), 2H; δ2.9–3.35(m), 4H; δ7.4(s), 1H.

EXAMPLE 17

2-tert-butyl-4-chloro-5-[4-(2,2-dimethylpropoxymethyl)cyclohexyl]methylthio-3(2H)-pyridazinone (compound 14)

Such compound (cis/trans 14/86 mixture) was prepared according to what is produced in the example 4 starting from 2-tert-butyl-4-chloro-5-mercapto-3(2H)-pyridazinone and 4-(2,2,-dimethylpropoxymethyl)-cyclohexylmethyl bromide.

$^1$H-NMR (60 MHz, CCl$_4$): δ0.6–2.2(m), 10H; δ0.85(s), 9H; δ1.55(s), 9H; δ2.85(m), 2H; δ2.9(s), 2H; δ3.1(m), 2H; δ7.4(bs), 1H.

EXAMPLE 18

2-tert-butyl-4-chloro-5-[4-(3-methylbutoxymethyl)cyclohexyl]methylthio-3(2H)-pyridazinone (compound 15)

Such compound (cis/trans 19/81 mixture) was prepared according to what is produced in the example 4 starting from 2-tert-butyl-4-chloro-5-mercapto-3(2H)-pyridazinone and 4-(3-methylbutoxymethyl)-cyclohexylmethyl bromide.

$^1$H-NMR (60 MHz, CCl$_4$): δ0.6–2.2(m), 13H; δ0.8(d), 6H; δ1.6(s), 9H; δ2.8(m), 2H; δ2.9–3.4(m), 4H; δ7.3(s), 1H.

EXAMPLE 19

2-tert-butyl-4-chloro-5-(4n-hexyloxymethylcyclohexyl) methylthio-3(2H)-pyridazinone (compound 16)

Such compound (cis/trans 1/4 mixture) was prepared according to what is produced in the example 4 starting from 2-tert-butyl-4-chloro-5-mercapto-3(2H)-pyridazinone and 4-n-hexyloxymethylcyclohexylmethyl bromide.

$^1$H-NMR (60 MHz, CCl$_4$): δ0.5–2.2(m), 21H; δ1.6(s), 9H; δ2.8(m), 2H; δ2.9–3.4(m), 4H; δ7.4(bs), 1H.

EXAMPLE 20

2-tert-butyl-4-chloro-5-(4-cyclohexyloxymethylcyclohexyl) methylthio-3(2H)-pyridazinone (compound 17)

Such compound (cis/trans 15/85 mixture) was prepared according to what is produced in the example 4 starting from 2-tert-butyl-4-chloro-5-mercapto-3(2H)-pyridazinone and 4-cyclohexyloxymethylcyclohexylmethyl bromide.

$^1$H-NMR (60 MHz, CCl$_4$): δ0.6–2.2(m), 20H; δ1.6(s), 9H; δ2.8(m), 2H; δ2.85–3.4(m), 3H; δ7.35(s), 1H.

EXAMPLE 21

2-tert-butyl-4-chloro-5-(4-cyclohexyloxymethylcyclohexyl) methylthio-3(2H)-pyridazinone (compound 18)

Such compound (cis/trans 15/85 mixture) was prepared according to what is produced in the example 4 starting from 2-tert-butyl-4-chloro-5-mercapto-3(2H)-pyridazinone and 4-cyclohexylmethoxymethylcyclohexylmethyl bromide.

$^1$H-NMR (60 MHz, CCl$_4$): δ0.6–2.2(m), 21H; δ1.6(s), 9H; δ2.8(m), 2H; δ2.9–3.2(m), 4H; δ7.4(s), 1H.

EXAMPLE 22

2-tert-butyl-4-chloro-5-(4-isobutylthiomethylcyclohexyl) methylthio-3(2H)-pyridazinone (compound 19)

Such compound (cis/trans 15/85 mixture) was prepared according to what is produced in the example 4 starting from 2-tert-butyl-4-chloro-5-mercapto-3(2H)-pyridazinone and 4-isobutylmethylcyclohexylmethyl bromide.

$^1$H-NMR (60 MHz, CCl$_4$): δ0.6–2.2(m), 11H; δ0.9(d), 6H; δ1.6(s), 9H; δ2.25(m), 4H; δ2.85(m), 2H; δ7.4(s), 1H.

EXAMPLE 23

2-tert-butyl-4-chloro-5-(4-methoxycyclohexyl)methylthio-3(2H)-pyridazinone (compound 20)

Such compound (cis/trans 65/35 mixture) was prepared according to what is produced in the example 4 starting from 2-tert-butyl-4-chloro-5-mercapto-3(2H)-pyridazinone and 4-methoxycyclohexylmethyl bromide.

$^1$H-NMR (60 MHz, CCl$_4$): δ0.9–2.2(m), 9H; δ1.6(s), 9H; δ2.85(m), 2H; δ3.25–3.3(2s), 3H; δ3.1–3.5(m), 1H; δ7.45(s), 1H.

EXAMPLE 24

2-tert-butyl-4-chloro-5-(4-ethoxycyclohexyl)methylthio-3(2H)-pyridazinone (compound 21)

Such compound (cis/trans 64/36 mixture) was prepared according to what is produced in the example 4 starting from 2-tert-butyl-4-chloro-5-mercapto-3(2H)-pyridazinone and 4-ethoxycyclohexylmethyl bromide.

$^1$H-NMR (60 MHz, CCl$_4$): δ0.9–2.2(m), 9H; δ1.1(t), 3H; δ1.6(s), 9H; δ2.85(m), 2H; δ3.1–3.5(m), 3H; δ7.45(s), 1H.

EXAMPLE 25

2-tert-butyl-4-chloro-5-(4n-propoxycyclohexyl)methylthio-3(2H)-pyridazinone (compound 22)

Such compound (cis/trans 65/35 mixture) was prepared according to what is produced in the example 4 starting from 2-tert-butyl-4-chloro-5-mercapto-3(2H)-pyridazinone and 4-n-propoxycyclohexylmethyl bromide. The mixture (0.5 g) was eluted, by chromatography on silica gel, with hexane/ethyl acetate 9:1 to give cis-isomer (0.25 g) and trans-isomer (0.15 g, m.p. 96° C.)

$^1$H-NMR cis-isomer (200 MHz, CDCl$_3$): δ0.92(t), 3H; δ1.35–1.75(m), 9H; δ1.65(s), 9H; δ1.83–1.97(m), 2H; δ2.93(d), 2H; δ3.35(t), 2H; δ3.47–3.57(m), 1H; δ7.45(s), 1H.

$^1$NMR trans-isomer (200 MHz, CDCl$_3$): δ0.92(t), 3H; δ0.97–1.37(m), 4H; δ1.47–1.73(m) 3H; δ1.65(s), 9H; δ1.93–2.18(m) 4H; δ2.9(d), 2H; δ3.10–3.27(m), 1H;δ3.42(t), 2H; δ7.45(s), 1H.

EXAMPLE 26

2-tert-butyl-4-chloro-5-(4-isopropoxycyclohexyl)methylthio-3(2H)-pyridazinone (compound 23)

Such compound (cis/trans 75/25 mixture) was prepared according to what is produced in the example 4 starting from 2-tert-butyl-4-chloro-5-mercapto-3(2H)-pyridazinone and 4-isopropoxycyclohexylmethyl bromide.

$^1$H-NMR (60 MHz, CCl$_4$): δ0.9–2.2(m), 10H; δ1.0(d), 6H; δ1.65(s), 9H; δ2.85(m), 2H; δ3.1–3.7(m), 2H; δ7.5(s), 1H.

EXAMPLE 27

2-tert-butyl-4-chloro-5-(4-isobutoxycyclohexyl)methylthio-3(2H)-pyridazinone (compound 24)

Such compound (cis/trans 64/36 mixture) was prepared according to what is produced in the example 4 starting from 2-tert-butyl-4-chloro-5-mercapto-3(2H)-pyridazinone and 4-isobutoxycyclohexylmethyl bromide.

$^1$H-NMR (60 MHz, CCl$_4$): δ0.9–2.2(m), 10H; δ0.85(d), 6H; δ1.6(m), 9H; δ2.8(m), 2H; δ3.0–3.5(m), 3H; δ7.45(s), 1H.

EXAMPLE 28

2-tert-butyl-4-chloro-5-[4-(3-methylbutoxy)cyclohexyl]methylthio-3(2H)-pyridazinone (compound 25)

Such compound (cis/trans 65/35 mixture) was prepared according to what is produced in the example 4 starting from 2-tert-butyl-4-chloro-5-mercapto-3(2H)-pyridazinone and 4-(3-methylbutoxy)cyclohexylmethyl bromide. The mixture (0.45 g) was eluted, by chromatography on silica gel, with hexane/ethyl acetate 9:1 to give cis-isomer (0.24 g) and trans-isomer (0.14 g, m.p. 81° C.)

$^1$H-NMR cis-isomer (200 MHz, CDCl$_3$): δ0.90(d), 6H; δ1.25–2.05(m), 12H; δ1.62(s), 9H; δ2.90(d), 2H; δ3.40(t), 2H; δ3.45–3.55(m), 1H; δ7.60(s), 1H.

$^1$H-NMR trans-isomer (200 MHz, CDCl$_3$): δ0.90(d), 6H; δ1.02–1.38(m), 4H; δ1.38–1.78(m), 4H; δ1.65(s), 9H; δ1.93–2.18(m), 4H; δ2.90(d), 2H; δ3.10–3.27(m), 1H; δ3.45(t), 2H;δ7.60(s), 1H.

EXAMPLE 29

2-tert-butyl-4-chloro-5-(4-n-propylcyclohexyl)methylthio-3(2H)-pyridazinone (compound 26)

Such compound (cis/trans 15/85 mixture) was prepared according to what is produced in the example 4 starting from 2-tert-butyl-4-chloro-5-mercapto-3(2H)-pyridazinone and 4-n-propylcyclohexylmethyl bromide.

$^1$H-NMR (200 MHz, CCl$_3$): δ0.9(t), 3H; δ0.80–2.10(m), 14H; δ1.65(s), 9H; δ2.85–3.05(m), 2H; δ7.6(s), 1H.

COMPARATIVE EXAMPLES 30 TO 32

The following compounds, specifically described or covered by patent application DE 3,733,220, were prepared:

Ex. 30) CR 1 = 2-tert.butyl-4-chloro-5-cyclopropylmethylthio-3(2H)-pyridazinone (corresponding to example 54).

Ex. 31) CR 2 = 2-tert.butyl-4-chloro-5-cyclohexylthio-3(2H)-pyridazinone (corresponding to example 128).

Ex. 32) CR 3 = 2-tert.butyl-4-chloro-5-cyclohexylmethylthio-3(2H)-pyridazinone.

The compounds were tested under the same conditions as are described in the following example 33. In the following Table we compare the results concerning such compounds with the ones obtained by using the compounds of the present invention.

EXAMPLE 33

Determination of the acaricide and insecticide action.

a) Acaricide action against Tetranychus urticae (T.U.; Acari).

Adults

Little discs obtained from bean leaves were infested with adult acari and then sprayed with a hydroacetonic solution (acetone: 10% by volume) of the product under test.

The death percentage was determined 48 hours after the treatment in comparison with the percentage of acari which infested discs sprayed only with a water solution at 10% of acetone.

Eggs

Little discs obtained from bean leaves were infested with acarus eggs and then treated by spraying a hydroacetonic solution of the product under test. The percentage of non-hatched eggs was evaluated 7 days after the treatment in comparison with the percentage of eggs which had been treated only with a hydroacetonic mixture.

b) Insecticide action against adults of Macrosiphum euphorbiae (M.E.; aphides). Potato plants cultivated in pot were infested with aphide adult females and, after a few hours, were sprayed with a hydroacetonic suspension (10% by volume of acetone) of the product under test.

The mortality percentage of the aphides was determined 24 hours after the treatment in comparison with the percentage of aphides, which infested plants treated only with an aqueous solution at 10% of acetone.

Complying with the forwarded procedures the compounds of the invention were tested in order to determine the acaricide and insecticide action.

The results of such determinations are reported in Table 1; said results are expressed as mortality percentage of the acari and insects treated with the compounds under test, at the indicated doses.

TABLE 1

| Compounds | T.U. adults 100 ppm 10 ppm | T.U. eggs 100 ppm 10 ppm | M.E. 100 ppm 10 ppm |
|---|---|---|---|
| 1 | 100 | 100 | 100 |
|   | 100 | 95 | 95 |

TABLE 1-continued

| Compounds | T.U. adults 100 ppm 10 ppm | T.U. eggs 100 ppm 10 ppm | M.E. 100 ppm 10 ppm |
|---|---|---|---|
| 2 | 100 | 100 | 100 |
|   | 90 | 94 | 100 |
| 3 | 100 | 100 | 100 |
|   | 30 | 65 | 76 |
| 4 | 100 | 100 | 100 |
|   | 50 | 40 | 97 |
| CR1 | 9* | 12* | 56 |
|   |   |   | 25 |
| CR2 | 11* | 17* | 75 |
|   |   |   | 26 |
| CR 3 | 16* | 30* | 100 |
|   |   |   | 65 |

*: 100 ppm

We claim:

1. 2-tert-butyl-4-chloro-5-(4-isobutoxymethyl-cyclohexyl)-methylthio-3(2)-pyridazinone.

2. A method of combatting acari and/or noxious insect infestations in agrarian, horticultural cultivations and/or in environments with by human beings and/or in domestic animals and cattle, consisting in applicating to the cultivation and/or in said ambients an effective amount of at least a pyridazinone having formula (I) of claim 1.

3. Compositions for combatting acari and/or noxious insect infestations, characterized in that they contain, besides one or more solid or liquid vehicles and besides other additives and/or other active substances and fertilizers, which are usual in the formulative field, at least a pyridazinone having formula (I) of claim 1.

* * * * *